United States Patent [19]

Goodman et al.

[11] Patent Number: 4,674,824
[45] Date of Patent: Jun. 23, 1987

[54] SYSTEM FOR ENHANCEMENT OF OPTICAL FEATURES

[75] Inventors: Joseph W. Goodman, Los Altos; Lambertus Hesselink, Woodside; Ellen Ochoa, Stanford, all of Calif.

[73] Assignee: Stanford University, Stanford, Calif.

[21] Appl. No.: 745,312

[22] Filed: Jun. 14, 1985

[51] Int. Cl.$^4$ .................. G03H 1/16; G03H 1/22; G02B 27/46
[52] U.S. Cl. ................................ 350/3.64; 350/3.85; 350/162.12
[58] Field of Search .............. 350/3.64, 162.12, 3.85

[56] References Cited

U.S. PATENT DOCUMENTS 4,453,804 6/1984 Evans ........................... 350/162.12
4,478,481 10/1984 Fusek et al. ...................... 350/3.85

*Primary Examiner*—Bruce Y. Arnold
*Attorney, Agent, or Firm*—Flehr, Hohbach, Test, Albritton & Herbert

[57] ABSTRACT

An optical system for selectively enhancing and/or suppressing the spectral intensity of components in an object beam, is disclosed. In one exemplary application, the optical system includes means for performing a forward transform operation on an input beam, a non-linear optical medium such as, for example, $Bi_{12}SiO_{20}$ or $Bi_{12}GeO_{20}$ and means for performing an inverse transform operation. In operation, the forward transform is performed on an input beam that contains a complex function characteristic of an object or subject, the resulting transform of the object beam is applied to the non-linear optical medium to form a hologram, then the hologram is read-out and the inverse transform operation is performed to provide an output optical beam that contains, for example, selectively enhanced intensity components and/or selectively suppressed intensity components. In one specific application, the object beam is obtained by transmitting a laser beam through a photomask such as, for example, the type used for fabricating semiconductor integrated circuits, the non-linear properties of the photorefractive crystal provide filtering or inversion of the intensity of the periodic aspects of the mask in the hologram and phase conjugate read-out and inverse transformation provide an image in which the intensity of the non-periodic defects is enhanced. In a second application, image inversion is employed to provide real-time inversion of intensity in the output image.

35 Claims, 7 Drawing Figures

SYSTEM FOR ENHANCEMENT OF OPTICAL FEATURES

The U.S. Government has rights in this invention pursuant to Contract No. AFOSR 83-0166 between the U.S. Department of the Air Force and Stanford University and pursuant to Grant No. DMR 83-16982 between the National Science Foundation and Stanford University.

BACKGROUND OF THE INVENTION

This invention relates to methods and apparatus for optical/digital inspection and to the suppression and enhancement of optical features. In one exemplary aspect, the present invention relates to the real-time suppression of periodic features and the enhancement of non-periodic defects, for example in the photomasks used in integrated circuit (IC) fabrication.

The present invention is described below with emphasis on the inspection of periodic grids or masks such as the photomasks used to pattern the etch and doping steps used in integrated circuit fabrication. In a particularly useful application, the technique is used to suppress the periodicity of IC masks and, at the same time, enhance or maximize the image intensity of non-periodic defects. However, as will be evident to those of skill in the art, the combination of Fourier optics and linear systems technology with nonlinear optics technology which is used for this defect enhancement is applicable in general to enhance and/or suppress the intensity of optical features.

The scale of integration of semiconductor devices on integrated circuit chips has improved greatly in the last several years. In fact, over the past five years, the silicon IC technology has grown from large scale integration (LSI) to very large scale integration (VLSI), and is expected to grow to ultra-large scale integration (ULSI) during the next several years. This continued improvement in silicon integrated circuit integration has been made possible in part by the apparatus used for lithography and etching. Generally, the density of integrated circuits and their speed of operation are dependent upon the accuracy and resolution of the lithography and etching apparatus which is used to form patterns of circuit elements in masking layers on the semiconductor wafer and then precisely replicate those patterns from the masking layers in the underlying semiconductor wafer layer(s). As the minimum lithographic feature size is decreased towards one micrometer and below, and as the device density increases accordingly, integrated circuits become increasingly susceptible to defects, including those resulting from the starting material and from the integrated processing sequence itself, and those which are transferred or replicated from the mask into the underlying semiconductor wafer layers. In fact, defect densities as low as one per square centimeter can result in unacceptably low integrated circuit processing yields.

In the past, digital techniques have been used for the inspection of two-dimensional fields such as integrated circuit masks. Generally, such techniques use a dual scanning microscope system and sophisticated algorithms for comparison and detection. Typically, however, such digital techniques are complicated and time consuming.

Unlike digital techniques, optical systems offer the advantage of parallel processing. Furthermore, there is no excessive requirement of accuracy in the output in terms of the actual intensity at each point. Rather, it is sufficient that the signal associated with a defect be much stronger than the signal associated with the surrounding periodic or quasi-periodic structure, so that, for example, a thresholding operation can be used to determine the defect location.

Optical spatial filtering techniques to perform defect enhancement have been examined in the past with regard to such applications as the inspection of electron beam collimating grids and silicon diode array targets for television camera tubes, as well as to the inspection of photomasks used in integrated circuit manufacture. The optical spatial filtering systems used a filter in the Fourier plane to attenuate the discrete spatial frequencies of the periodic portion of the mask, so that, upon retransformation only defects were present in the output. While the results of such systems were promising, the usefulness of the technique was limited by the fabrication time of the filter, and by the need to use high quality, low f number lenses when inspecting objects of large dimensions.

Recently, this second constraint has been removed by employing holographic recording of the output combined with phase-conjugate read-out. See, for example, R. L. Fusek, et al, "Holographic Optical Processing for SubMicron Defect Detection", Proceedings of the SPIE, Vol. 523, January, 1985. A three-step process is involved, however: first, a photographic filter is made, recording the Fourier spectrum of a mask to be tested; second, a hologram of the mask is recorded in the output plane using the filter to block the periodic portion of the spectrum; and finally, after processing the hologram is illuminated by the phase-conjugate of the reference beam and the defect-enhanced image is found in the output plane. This method has been used to detect submicron defects. However, it has the disadvantage, in addition to the above-mentioned requirement of a three-step process, that the process must be tailored to each mask and type of mask. That is, a new hologram must be recorded for each mask to be inspected and a new filter must be made for each type of mask.

SUMMARY OF THE INVENTION

In view of the above discussion, it is one object of the present invention to provide a technology for selectively enhancing and suppressing optical features.

It is also an object to provide a technology for suppressing periodic features, while simultaneously enhancing non-periodic features such as defects in periodic and quasi-periodic structures.

It is also an object of the present invention to provide apparatus and a method for enhancing defects in periodic and quasi-periodic structures which operate in real-time. Holographic recording, filtering, and read-out processes can be performed simultaneously or sequentially, using the same apparatus for different masks and different types of masks.

In one general aspect of the present invention, real-time selective image suppression and enhancement is provided by using a non-linear optical medium to effect interference between an incident reference beam and the transform of an object beam, to form a hologram in the medium, then reading out the hologram and performing an inverse transform operation on the output beam. Upon inverse transformation, the output contains selectively enhanced and/or suppressed input features. This technique is applicable to suppress or enhance essentially any selected input feature and is adaptable to various types of transform operations, including, but not limited to, Fourier transforms.

In one aspect which uses imaging rather than Fourier transforms, the present invention relates to the real-time inversion of intensity in images. Such inversion is obtained by imaging an object onto a non-linear medium such as a photorefractive crystal, and using a reference beam intensity that is weak by comparison with the object beam intensity. Under such conditions, the local diffraction efficiency from the crystal is inversely proportional to the local object intensity. Essentially any two-dimensional image can be inverted by this imaging process.

In one aspect which uses Fourier transforms, the present invention relates to non-linear filtering or suppression operations using a photorefractive crystal which is located in the Fourier domain. The transform of the object beam is focused onto the crystal, along with a reference beam of lower intensity than the peak values in the Fourier transform of the object beam. In the Fourier domain, the spectrum of the periodic or quasi-periodic structure consists of a series of bright and sharp Fourier components, corresponding to the harmonics of the periodic object such as a photomask. Also present in the Fourier domain are much broader and much weaker contributions of light corresponding to small defects in the periodic structure. Intensity inversion in the photorefractive crystal suppresses the strength of the bright spikes from the periodic components, in comparison to the strength of the weaker light from the defects. In general, the present invention provides the capability to enhance selected features or suppress selected features or to enhance selected features while suppressing others. The application of a read-out beam which, typically, is the phase conjugate of the reference beam, provides an image consisting primarily of the defects, with the periodicities missing or greatly reduced in intensity. This enhancement process takes place in real-time, in the sense that the mask or other object is introduced at the input and, within a short time, such as a few milliseconds, an image of the defects appears.

This nonlinear filtering technique has many other applications. These include, for example, in addition to the inspection applications mentioned previously, the industrial inspection of meshes used in chemistry and biology, and the inspection of shadow grids used in color TV tubes.

Additional suitable nonlinear optical media include other photorefractives, ferroelectrics, organic/inorganic materials exhibiting second and third order nonlinear susceptibilities, materials exhibiting resonant transitions and semiconductor materials.

DETAILED DESCRIPTION OF A PREFERRED EMBODIMENT OF THE INVENTION

Figure 1:
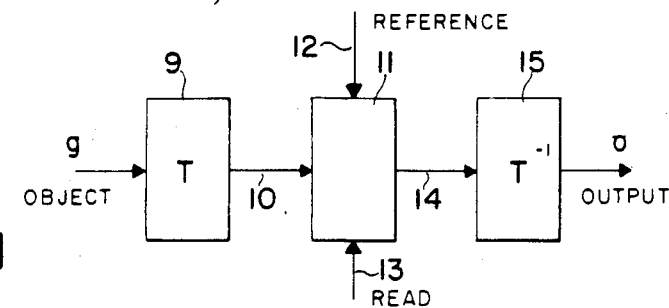
FIG. 1 is a block diagram which illustrates the operations performed on an object beam according to one aspect of the present invention, namely, forward transform, hologram generation with beam component enhancement and/or suppression, inverse transform and read-out.

FIG. 1 is a simplified block diagram which schematically illustrates the basic aspects of one embodiment of the present invention. Initially, a transform operation is applied as indicated at 9, such as, for example, using Fourier optics, to perform a forward transform operation on an input beam which contains a complex function, g, characteristic of an object or subject. The resulting Fourier transform 10 of the object beam is applied to a nonlinear optical medium, 11, and there interferes with a reference beam 12 to form a hologram in the medium. Then, the hologram is read-out by beam 13 and an inverse transform operation is performed on the output beam 14, as indicated at 15, to provide an output, o, in the form of an optical beam which contains, for example, selectively enhanced intensity components and/or selectively suppressed intensity components.

Figure 3:
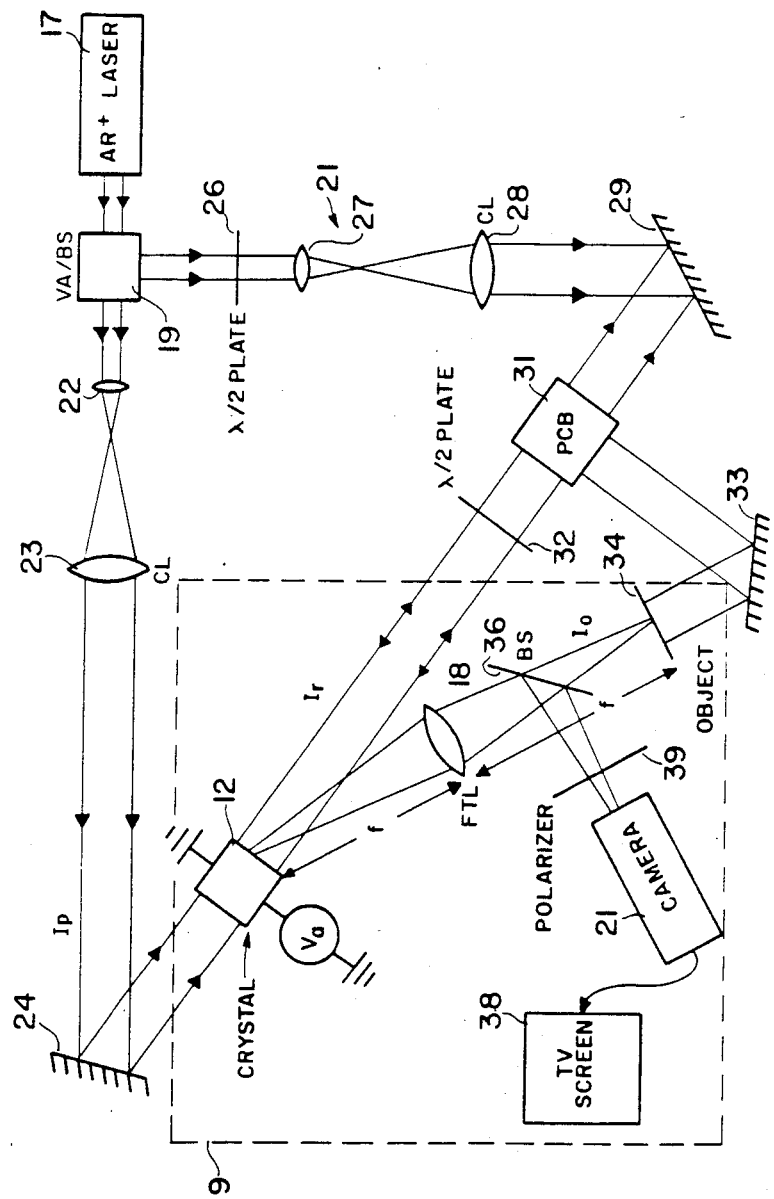
FIG. 3 is a block diagram of one embodiment of the present invention, namely an optical defect enhancement system.

In one specific application, described in detail with respect to FIG. 3, the object beam is obtained by transmitting a laser beam through a photomask of the type used for the fabrication of semiconductor integrated circuits. The nonlinear medium is a photorefractive crystal, whose nonlinear properties provide filtering or inversion of the intensity of the periodic aspects of the mask in the hologram. Phase-conjugate read-out (four-wave mixing) and inverse transformation provide an image in which the intensity of non-periodic defects is enhanced.

Our technique and system for performing real-time defect enhancement is based on two observations. The first is that the Fourier transform of a periodic object is an array of discrete spikes whose width depends inversely on the input field size and whose spacing depends inversely on the period of the mask. In contrast, the Fourier transform of a small defect is a continuous function which is several orders of magnitude less intense than the periodic spikes. It should be noted that other transforms may be used, such as the Mellin transform, to achieve similar results. The second observation is that the diffraction efficiency of a volume phase hologram formed in a photorefractive medium is maximized when the intensities of the two writing beams are approximately equal and decreases as the difference in intensity increases. For a reference plane wave having intensity, $I_r$, greater than the intensity, $I_o$, of the object beam, the output is proportional to the object beam intensity; for an object beam more intense than the reference beam, the output is proportional to the inverse of the intensity of the object beam. It should be noted that for operation of the device it is necessary to have a third beam incident in the crystal to produce the desired output signal. This beam may be applied simultaneously with the other beams or may be applied sequentially, after writing the hologram.

Figure 2:
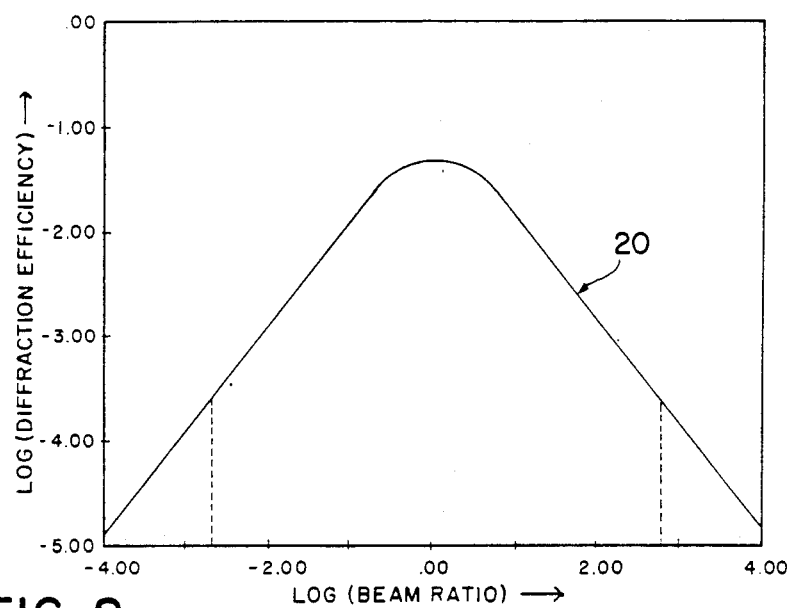
FIG. 2 is a typical curve of log (diffraction intensity) versus log ($I_o/I_r$ beam ratio) for photorefractive $Bi_{12}SiO_{20}$ (BSO) or $Bi_{12}GeO_{20}$ (BGO)

A typical diffraction efficiency versus beam ratio curve 20 is plotted in FIG. 2 on a log-log scale, assuming that the beam ratio, $R (\equiv I_o/I_r)$ is varied by changing $I_o$ while keeping $I_r$ fixed. A defect can be enhanced by focusing the Fourier transform of a mask onto the photorefractive crystal and making the intensity of the peak spectral component due to the defect close to or less than the intensity of the reference beam. The beam ratio of the defect spectrum intensity to the reference beam intensity should, thus, be <1. The intensity of the spikes due to the periodic structure will be so much greater than the reference beam intensity, that the corresponding diffraction efficiency will be very small. Thus, the refractive index pattern formed inside the crystal performs both recording and filtering operations.

A Fourier optics analysis can be used to describe the propagation of light from the object to the crystal. Suppose the mask is rectangular with dimension W×L and a small transparent rectangular defect, located at $(x_o, y_o)$, has dimensions w×l. Let p (x,y) represent one unit cell of the periodic structure, which is spaced at intervals of length a. The intensity of the Fourier transform at the crystal, assuming W,L >> a and unit illumination, is $$|T(u,v)|^2 = \frac{1}{(\lambda f)^2} [F], \text{ where} \qquad (1)$$

$$[F] = \left[ (WL)^2 \frac{1}{a^4} \sum_n \sum_m P^2\left(\frac{n}{a}, \frac{m}{a}\right) \text{sinc}^2\left(W\left(u - \frac{n}{a}\right)\right) \text{sinc}^2\left(L\left(v - \frac{m}{a}\right)\right) + (wl)^2 \text{sinc}^2(wu)\text{sinc}^2(lv) \right],$$

and where the sinc function is as defined in Bracewell, "The Fourier Transform and its Applications", McGraw-Hill, Inc., New York, 1978. Bracewell is incorporated by reference. The spatial frequency variables are related to spatial variables as $u=x/\lambda f$ and P(u,v) is the Fourier transform of p(x,y). P(0,0) represents the transmitting area of one period of the pattern, and $P(0,0)/a^2$ is the fraction of the mask area that is transmitting.

The hologram should be recorded such that the intensity of the periodic portion of $|T(u,v)|^2$ is greater than the reference beam intensity, and the intensity of the defect portion of $|T(u,v)|^2$ is less than the reference beam intensity. Mathematically, if D is defined as the relevant dynamic range of the periodic portion and the light incident on the mask is $I_i$, then $$I_i(WL/\lambda f)^2 P^2(0,0)/a^4(1/D) > I_r; \qquad (2)$$

$$I_i(wl/\lambda f)^2 < I_r. \qquad (3)$$

The second result, i.e., relationship (3) applies to a transmitting defect and the result needs to be modified to $$I_i(wl/\lambda f)^2 \left| 1/a^2 \sum_n \sum_m P(n/a, m/a) \text{sinc}(ln/a)\text{sinc}(wm/a) \right|^2 < I_r, \qquad (3a)$$

for an opaque defect.

Mask Defect Enhancement Example

One example of a system used to obtain defect enhancement is shown in FIG. 3. The critical portion of the system, i.e., that portion corresponding generally to the system shown in FIG. 1, is identified by block 9. An Argon ion laser 17 ($\lambda=514.5$ nm) was collimated and split to form the two writing beams, i.e., the reference beam and the object beam, as well as the probe (read-out) beam. Here, $I_r$ denotes the relatively low intensity reference beam, $I_o$ denotes the object beam and $I_p$ denotes the read-out beam. Both $Bi_{12}GeO_{20}$ (BGO) and $Bi_{12}SiO_{20}$ (BSO) crystals 12 were used. In this exemplary case, a $Bi_{12}SiO_{20}$ (BSO) crystal 12, of size $8\times8\times8$ mm$^3$, was oriented with the x-direction along a [110] axis. Both the object beam and the reference were incident on the crystal 12 at an angle of about 7.5° relative to the normal to the crystal surface to form an index of refraction grating within the crystal. The read-out beam was directed at the Bragg angle of about 7.5° relative to the normal to the opposite face of the crystal relative to the writing beams. A lens 18 of focal length 381 mm and diameter 78 mm was used to perform the Fourier transform and the inverse transform, and the output was detected by a CCD camera 21.

Considering FIG. 3 further, the coherent radiation from the argon ion laser 17 was split by a variable attenuator/beam splitter 19 into a first beam, the phase-conjugate read-out beam $I_p$, and a second beam, designated generally 21. The variable attenuator/beam splitter 19 was also used to control the intensity of the read-out beam relative to the second beam 22, that is, to provide a relatively low intensity read-out beam. The probe or read-out beam $I_p$ was expanded by converging lens 22 and collimated by lens 23, then directed by mirror 24 onto the crystal under Bragg conditions. The second beam 21 traveled through a half-wave plate 26 then was expanded by lens 27 and collimated by lens 28. The second wave 21 was then directed by a mirror 29 to a polarizing cube beam splitter 31 for splitting the second beam. One of the resulting beams was transmitted through half-wave plate 32 to provide the reference wave $I_r$. The other resulting beam, object wave $I_o$, was directed by mirror 33 onto the object 34, in this case a periodic mask, then to the lens 18, which performed the forward Fourier transform operation on the object beam. The transform of the object beam was focused onto the photorefractive crystal 12, where interference between the reference wave $I_r$ and the transform of the object beam $I_o$ formed a hologram of the Fourier transform of the object 36. The combination of half-wave plate 26, polarizing cube beam splitter 31 and second half-wave plate 32 allowed the beam ratio $I_o/I_r$ to be changed to provide the desired relatively low intensity reference beam while keeping the polarization the same.

It should be noted that the object 34 was at the front focal plane of the Fourier transform lens (this is not a necessary condition, as the object could be placed anywhere in front of the lens), whereas the crystal was at the back focal plane. Read-out was provided by the phase-conjugate beam $I_p$. The output traversed lens 18, where the inverse transform operation was performed, then was directed by beam splitter 36 to camera 21. In the particular set-up shown in FIG. 3, the output was detected at camera 21, which was a CCD (charged coupled device) camera, and was displayed by a standard TV screen or monitor 38. A polarizer 39 was placed in front of the output to reduce scatter light and increase the signal-to-noise ratio. It should be noted that suitable detectors other than a CCD camera can be used. Also, other photorefractive and nonlinear optics materials in general, can be used. Also, while the FIG.

3 exemplary system uses a transmissive geometry, in which the laser light is transmitted through object 34, one could also use a reflective geometry in which the object beam $I_o$ is generated by reflection from the object. It should be noted that the read-out and writing beams could be derived from different sources.

Figure 5:
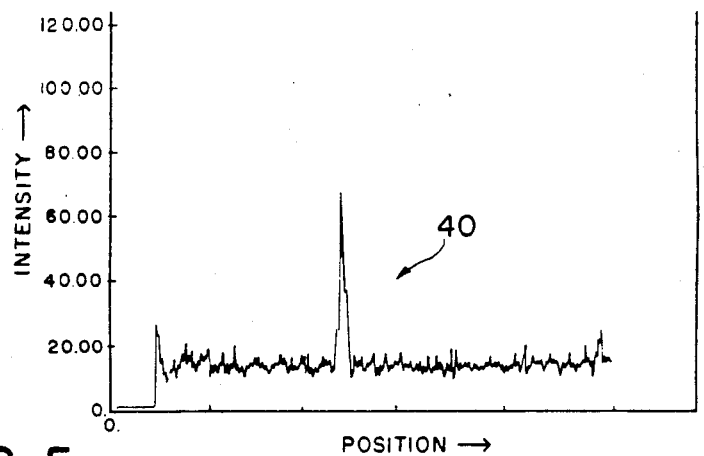
FIG. 5 is a graph of the intensity line scan illustrating the signal-to-noise ratio for the smallest defect of FIGS. 4A and 4B.
Figure 4B:
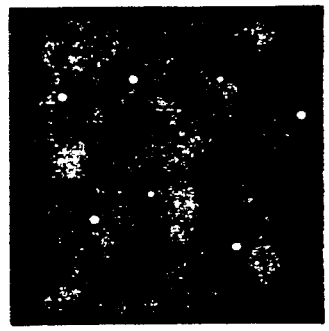
FIGS. 4A and 4B illustrate, respectively, a periodic mask containing defects and the defect-enhanced optical read-out of the mask which is provided by the system of FIG. 3.
Figure 4A:
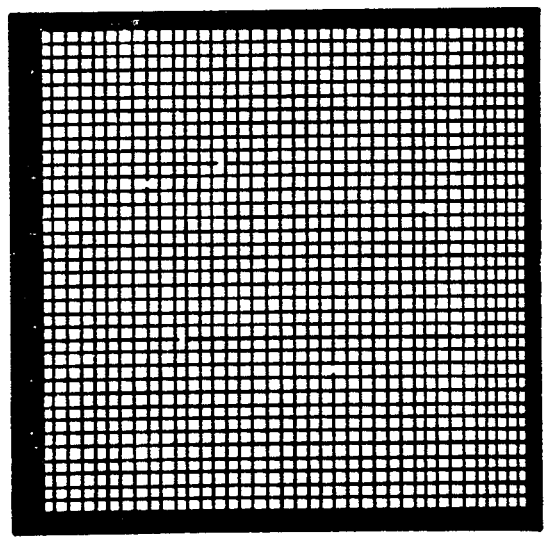

The object mask 16 consisted of a 36×36 array of squares, each with sides of 150 μm (micrometer). The spacing between the squares was 100 μm, so the period a was equal to 250 μm. The total mask size was 9×9 mm². Within this array were placed seven transmitting defects of sizes 100×100 μm², 100×50 μm² (two defects), 100×25 μm² (two defects), and 100×10 μm² (two defects), as shown in FIG. 4A. The output of the optical system is shown in FIG. 4B, obtained using an applied voltage of 4 kV across the crystal. Please note—the two smallest defects are not visible in FIG. 4A; they do appear in the output of FIG. 4B, however. In FIG. 4B, the periodic background has been quite effectively suppressed, leaving the defects clearly visible. FIG. 5 shows an intensity scan of one line of the output image, illustrating the worst-case signal-to-noise ratio obtained. The defect represented is one of the two 10×100 μm² spots. The system is easily capable of detecting even smaller defects.

In recording the hologram, the object beam intensity at the mask ($I_o$) was 16 mW/cm² and the reference beam intensity ($I_r$) was 3.0 mW/cm² which led to beam ratios at the crystal (for the defect alone) of 0.014 to 0.00014, depending on the size of the defect. Thus, the experimental results indicate that enhancement occurs even for values of R much less than one. As a result, the incident beam ratio at the mask needed to obtain a defect-enhanced output ($I_o/I_r$) did not vary much in response to a range of defect areas of more than two orders of magnitude. Because the inverse properties shown in FIG. 1 were derived under conditions of plane wave illumination, the filtering properties of the crystal cannot be described by simply a beam ratio dependence. The ratio of the peak of the periodic portion of the transform to the peak of the defect portion ranged from $8.5 \times 10^6$ to $8.5 \times 10^8$.

The resolution obtained in the output can be increased by, for instance, reducing the f# of the optical system (and using a crystal of larger dimensions), by increasing the size of the imaging elements of the CCD camera, (each of which measured 23 μm×13.4 μm), and/or by using other nonlinear recording materials.

Intensity Inversion

Figure 6:
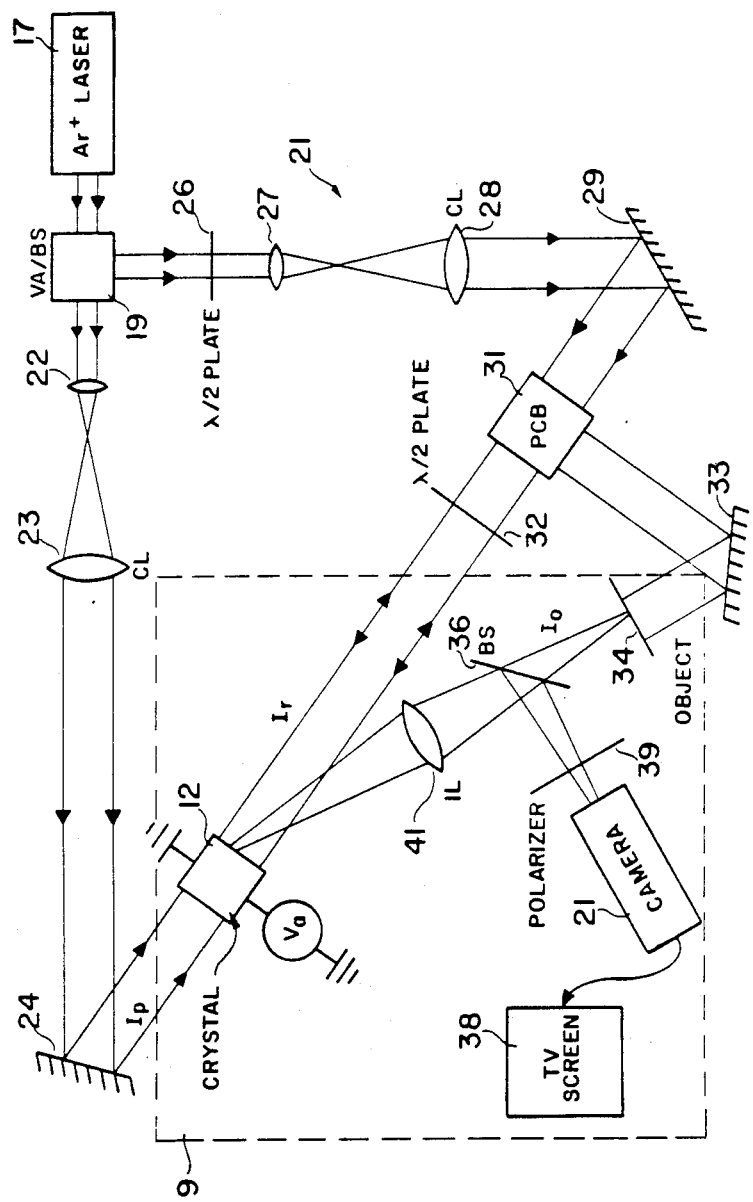
FIG. 6 is a block diagram of an alternative embodiment of the present invention in the form of a system for performing optical intensity inversion.

A second application of the present invention, to real-time, image inversion is illustrated in FIG. 6. The four-wave mixing system shown in FIG. 6 was basically similar to that of FIG. 3, except that an imaging lens 41 was used rather than the Fourier transform lens 18 of FIG. 3. Thus, the crystal 12 was located in the image domain, rather than in the Fourier domain, as was the case for the FIG. 3 system, and the forward and inverse transformations using lens 41 involves imaging rather than Fourier transformations. This technique was similar to that of FIG. 3 in that the object was imaged onto the crystal using a reference beam intensity that is weak by comparison with the object beam intensity. Under such imaging conditions, the local diffraction efficiency from the crystal is inversely proportional to the local object intensity, thereby providing real-time inversion of intensity in the output image.

While the above intensity inversion and defect examples illustrate application of the invention using the visible portion of the electromagnetic spectrum, the invention is applicable as well to the other, invisible portions of the electromagnetic spectrum, such as, for example, to X-rays.

In summary, a technology for selectively enhancing and/or suppressing optical features in real-time has been presented. Specific systems for the enhancement of non-periodic features and for image inversion have been described, as well as bases for extending the invention to other suppression/enhancement applications using Fourier and other types of transforms.

We claim:

1. An optical system for forming, from an object beam of electromagnetic radiation, a hologram characterized by selectively altered intensity of the components in the object beam, comprising: a nonlinear optical medium for selectively altering the intensity of components in an incident object beam; means for performing forward and inverse transform operations on incident beams of electromagnetic radiation; and means for (a) transmitting said object beam through the transform means to thereby direct the forward transform of said object beam onto the nonlinear optical medium and (b) simultaneously directing a reference beam of electromagnetic radiation onto the nonlinear optical medium to form a hologram of the object beam transform therein.

2. The optical system of claim 1, further comprising means for applying a read-out beam of electromagnetic radiation to the nonlinear optical medium to thereby provide an output beam directed from the hologram to the transform means to form an optical output which is the inverse transform of the output beam from the hologram and is characterized by the selectively altered intensity of the components therein.

3. The optical system of claim 1 or 2, wherein the radiation is from the visible portion of the electromagnetic spectrum.

4. The optical system of claim 1 or 2, wherein the radiation is coherent light.

5. The optical system of claim 1 or 2, wherein the radiation is laser light.

6. The optical system of claim 1 or 2, wherein the radiation is from the invisible portion of the electromagnetic spectrum.

7. The optical system of claim 2, wherein the means for applying the read-out beam applies the read-out beam substantially simultaneously with the hologram formation.

8. The optical system of claim 2, wherein the means for applying the read-out beam applies the read-out beam sequentially to the hologram formation.

9. The optical system of claim 1, further comprising means for converting the optical output to an image.

10. The optical system of claim 9, further comprising means for recording the image.

11. The optical system of claim 1, wherein the nonlinear optical medium is a photorefractive crystal.

12. The optical system of claim 1, wherein the nonlinear optical medium is $Bi_{12}SiO_{20}$.

13. The optical system of claim 1, wherein the nonlinear optical medium is $Bi_{12}GeO_{20}$.

14. The optical system of claim 11, 12 or 13, wherein: the transform means is an optical imaging lens and the object and the nonlinear optical medium are positioned, respectively, at an object plane and at the corresponding image plane of the lens.

15. The optical system of claim 11, 12 or 13, wherein: the transform means is a Fourier transform lens and the object and the nonlinear optical medium are positioned, respectively, at the front focal plane and the back focal plane of the lens.

16. An optical system for selectively altering the intensity of optical components in an object beam, comprising: a nonlinear optical medium suitable for selectively altering the intensity of optical components in an incident light beam; means for performing a forward and an inverse transform operation on incident optical beams; means for (a) transmitting the object beam through the transform means to thereby direct the forward transform of the object beam onto the nonlinear optical medium and (b) simultaneously directing a reference light beam onto the nonlinear optical medium to form a hologram of the object beam transform therein; and means for applying a read-out light beam to the nonlinear optical medium to direct an output beam from the hologram to the transform means to form an optical output which is an inverse transform of the output beam from the hologram and is characterized by the selectively altered intensity of the components therein.

17. The optical system of claim 16, further comprising means for converting the optical output to an image.

18. The optical system of claim 17, further comprising means for recording the image.

19. The optical system of claim 16, wherein the nonlinear optical medium is a photorefractive crystal.

20. The optical system of claim 16, wherein the nonlinear optical medium is $Bi_{12}SiO_{20}$.

21. The optical system of claim 16, wherein the nonlinear optical medium is $Bi_{12}GeO_{20}$.

22. The optical system of claim 19, 20, or 21, wherein: the transform means is an optical imaging lens and the object and the nonlinear optical medium are positioned, respectively, at an object plane and at the corresponding image plane of the lens.

23. The optical system of claim 19, 20 or 21, wherein: the transform means is a Fourier transform lens and the object and the nonlinear optical medium are positioned, respectively, at the front focal plane and the back focal plane of the lens.

24. The optical system of claim 16, wherein said object, reference and read-out beams are coherent.

25. The optical system of claim 16, wherein said object, reference and read-out beams are laser light.

26. The optical system of claim 16, wherein the means for applying the read-out beam applies the read-out beam substantially simultaneously with the hologram formation.

27. The optical system of claim 16, wherein the means for applying the read-out beam applies the read-out beam sequentially to the hologram formation.

28. A system for providing enhanced real-time optical intensity of non-periodic components in a periodic two-dimensional object structure, comprising: a nonlinear optical medium; means for providing a coherent light beam; means for separating the coherent beam into a first, relatively low intensity read-out beam and a second beam; means for separating the second beam into an object beam and also into a reference beam of low intensity relative to the object beam directly onto the optical medium; a Fourier transform lens positioned with the periodic structure at the front focal plane thereof and the optical medium at the back focal plane thereof for directing the forward Fourier transform of the object beam onto the optical medium such that interference between the relatively low intensity reference beam and the forward Fourier transform provides a hologram in the optical medium; and means for providing a coherent probe light beam for reading out the hologram via the Fourier transform lens to provide an optical output which is the inverse transform of the output beam from the hologram and is characterized by enhanced intensity of the non-periodic components.

29. The optical system of claim 28, further comprising means for converting the optical output to an image.

30. The optical system of claim 29, further comprising means for recording the image.

31. The optical system of claim 29, wherein the optical medium is $B_{12}SiO_{20}$.

32. The optical system of claim 29, wherein the optical medium is $Bi_{12}GeO_{20}$.

33. The optical system of claim 28, wherein the means for applying the probe beam applies the probe beam substantially simultaneously with the hologram formation.

34. The optical system of claim 28, wherein the means for providing the probe beam applies the probe beam sequentially to the hologram formation.

35. The optical system of claim 28, wherein the object structure is a photomask containing a periodic array of transparent and non-transparent components and wherein the relative intensity of the reference and object beams is selected to enhance the intensity of the selected non-periodic components in the mask relative to that of the periodic components.

* * * * *

UNITED STATES PATENT AND TRADEMARK OFFICE
CERTIFICATE OF CORRECTION

PATENT NO. : 4,674,824
DATED : June 23, 1987
INVENTOR(S) : Joseph W. Goodman, et al It is certified that error appears in the above-indentified patent and that said Letters Patent is hereby corrected as shown below:

Column 1, line 4, after the title, insert the following paragraph:

--This invention was made with Government support under contracts DMR-83-16982 and AFOSR-83-0166 awarded by the National Science Foundation and the Department of the Air Force, respectively. The Government has certain rights in this invention.--

Signed and Sealed this

Tenth Day of January, 1995

*Attest:*

BRUCE LEHMAN

*Attesting Officer*   *Commissioner of Patents and Trademarks*